United States Patent [19]

Heaney et al.

[11] Patent Number: 4,752,321

[45] Date of Patent: Jun. 21, 1988

[54] BENZOYLAMINOMETHYLPYRAZOLES AND -FURANS, COMPOSITION CONTAINING THEM, AND FUNGICIDAL AND PLANT GROWTH REGULATING METHOD OF USING THEM

[75] Inventors: Stephen P. Heaney, Maidenhead; Patrick J. Crowley, Crowthorne; Laurence G. Reynolds, Camberley, all of England

[73] Assignee: Imperial Chemical Industries PLC, London, England

[21] Appl. No.: 932,102

[22] Filed: Nov. 18, 1986

[30] Foreign Application Priority Data

Dec. 5, 1985 [GB] United Kingdom ............... 8530015

[51] Int. Cl.⁴ .................. A01N 43/08; A01N 43/56; C07D 231/12; C07D 307/54
[52] U.S. Cl. ............................ 71/88; 71/92; 514/406; 514/471; 548/110; 548/378; 549/214; 549/493; 564/74; 564/186
[58] Field of Search ............... 548/110, 378; 549/493, 549/214; 514/406, 471; 71/92, 88

[56] References Cited

U.S. PATENT DOCUMENTS

| | | | |
|---|---|---|---|
| 4,432,784 | 2/1984 | Kay et al. | 549/493 |
| 4,447,446 | 5/1984 | Kay et al. | 549/436 |
| 4,515,959 | 5/1985 | Kay et al. | 548/378 |
| 4,552,887 | 11/1985 | Kay et al. | 514/381 |
| 4,663,481 | 5/1987 | Jones | 549/436 |

FOREIGN PATENT DOCUMENTS

| | | | |
|---|---|---|---|
| 0061836 | 10/1982 | European Pat. Off. | 549/436 |
| 0076030 | 4/1983 | European Pat. Off. | 549/493 |
| 0171768 | 2/1986 | European Pat. Off. | 549/436 |
| 0174088 | 3/1986 | European Pat. Off. | 548/378 |

*Primary Examiner*—Richard A. Schwartz
*Assistant Examiner*—Kurt G. Briscoe
*Attorney, Agent, or Firm*—Cushman, Darby & Cushman

[57] ABSTRACT

A compound of the general formula (I):

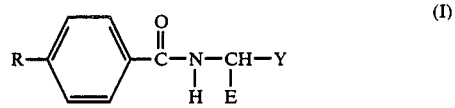

wherein R is $C_2$–$C_4$ alkenyl or $C_2$–$C_4$ alkynyl, both optionally substituted by lower alkyl, halogen or trialkylsilyl; E is CN or $CSHN_2$; and Y is $C_1$–$C_4$ alkoxy, $C_3$–$C_4$ alkenyloxy, $C_3$–$C_4$ alkynyloxy, 1-pyrazolyl or 2-furyl. The compounds have fungicidal and plant growth regulating activity.

6 Claims, No Drawings

BENZOYLAMINOMETHYLPYRAZOLES AND -FURANS, COMPOSITION CONTAINING THEM, AND FUNGICIDAL AND PLANT GROWTH REGULATING METHOD OF USING THEM

This invention relates to substituted benzamide derivatives useful as fungicides and plant growth regulators, to processes for preparing them, to compositions containing them and to methods of combating fungal infestations, particularly plant fungal diseases, and of regulating plant growth using them.

Certain substituted benzamide derivatives, for example those disclosed in European Patent Publications Nos. 59536, 61836 and 76030, have previously been proposed for use as fungicides.

According to the present invention there are provided novel benzamide derivatives of the general formula (I):

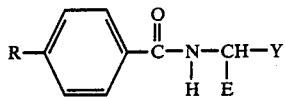

wherein
R is $C_2$-$C_4$ alkenyl or $C_2$-$C_4$ alkynyl, both optionally substituted by lower alkyl, halogen or trialkylsilyl;
E is CN or $CSNH_2$; and
Y is $C_1$-$C_4$ alkoxy, $C_3$-$C_4$ alkenyloxy, $C_3$-$C_4$ alkynyloxy, 1-pyrazolyl or 2-furyl.

General formula (I) is believed to be the one which best represents the structure of the compounds. It is, of course, conceivable that some of the compounds exist in a tautomeric form; for instance, they could have the alternative formula (II):

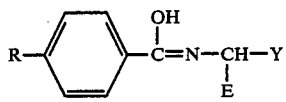

The general formula (I) is, however, intended to represent and include such tautomeric forms, insofar as they may exist. Formula (I) is also intended to include any physically distinguishable modifications of the compounds which may arise, for example, from different ways in which the molecules are arranged in a crystal lattice, or from the inability of parts of the molecules to rotate freely in relation to other parts, or from geometrical and or optical isomerism, or from intramolecular or intermolecular bonding, or otherwise. In particular, the compounds contain an asymmetric carbon atom and are therefore capable of existing in two optically isomeric (enantiomeric) forms. The present invention includes the dextro- and laevo-rotatory isomers of each compound and their mixtures in all proportions including mixtures which comprise predominantly the dextro-isomer and those which comprise predominantly the laevo-isomer. Such isomers have different fungicidal activity.

When R is $C_2$-$C_4$ alkenyl it is preferably 1-($C_2$-$C_4$) alkenyl, especially ethenyl or prop-1-enyl; and when R is $C_2$-$C_4$ alkynyl it is preferably 1-($C_2$-$C_4$) alkynyl especially ethynyl or prop-1-ynyl. The $C_2$-$C_4$ alkenyl and $C_2$-$C_4$ alkynyl groups may be substituted by lower alkyl, halogen or trialkylsilyl. A preferred substituent of $C_2$-$C_4$ alkynyl is trialkylsilyl, especially trimethylsilyl, and of particular interest as a value of R is trimethylsilylethynyl.

The term lower alkyl is intended to mean alkyl groups containing from 1 to 6, especially 1 to 4, carbon atoms, e.g. methyl, ethyl, propyl (-n and isopropyl) and butyl (n, iso, sec and t-butyl). This applies to alkyl groups and alkyl moieties of trialkysilyl groups.

Preferred values of Y are 1-pyrazolyl, 2-furyl, ethoxy, allyloxy and propargyloxy.

Preferred compounds are those in which R is 1-($C_2$-$C_4$) alkynyl, especially ethynyl optionally substituted by trimethylsilyl, and prop-1-ynyl, Y is ethoxy or 1-pyrazolyl, and E is CN.

The term halogen includes fluorine, chlorine, bromine and iodine but preferred halogen substituents are bromine and iodine.

The invention is illustrated by the compounds of general formula (I) in which the values of R, E and Y are set out in Table I below.

TABLE I

| Compound No | R | E | Y | mpt °C. |
|---|---|---|---|---|
| 1 | HC≡C | CN | 1-pyrazolyl | 164–166 |
| 2 | $CH_3$C≡C | CN | 1-pyrazolyl | 185–187 |
| 3 | $(CH_3)_3$SiC≡C | CN | 1-pyrazolyl | 216–21 |
| 4 | HC≡C | CN | ethoxy | 104–106 |
| 5 | $(CH_3)_3$SiC≡C | CN | ethoxy | 134–136 |
| 6 | $CH_3$C≡C | CN | ethoxy | 118–120 |
| 7 | $(CH_3)_3$SiC≡C | CN | 2-furyl | |
| 8 | HC≡C | CN | 2-furyl | 123–126 |
| 9 | $CH_3$C≡C | CN | 2-furyl | |
| 10 | $CH_3$C≡C | $CSNH_2$ | 1-pyrazolyl | |
| 11 | HC≡C | $CSNH_2$ | ethoxy | |
| 12 | HC≡C | $CSNH_2$ | 1-pyrazolyl | 145 |
| 13 | $CH_2$=CH | CN | 1-pyrazolyl | 159–161 |
| 14 | $CH_2$=CH | CN | ethoxy | |
| 15 | $CH_2$=CH | CN | 2-furyl | |
| 16 | $CH_2$=CH | $CSNH_2$ | ethoxy | |
| 17 | $CH_3$CH=CH | CN | 1-pyrazolyl | |
| 18 | $CH_3$CH=CH | CN | ethoxy | |
| 19 | HC≡C | CN | propargyloxy | |
| 20 | HC≡C | CN | allyloxy | |

The invention further provides processes for preparing compounds of formula (I) above. Thus the compounds wherein R is 1-alkynyl (reading from the ring) may be prepared, for example, by the process of Scheme A below:

Scheme A

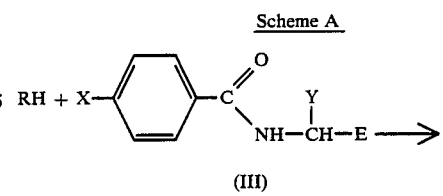

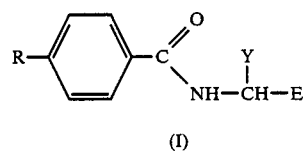

A compound of formula (I) where R is a 1-alkynyl group e.g. the group:

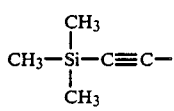

may be produced in one step, by reaction of an alkyne (RH) with a compound of formula (III), where X is bromine or iodine (but preferably iodine) in the presence of a palladium catalyst such as Pd (Ph$_3$P)$_4$, and a monovalent copper salt such as cuprous iodide, in an amine solvent such as diethylamine or triethylamine (preferably triethylamine) at a temperature of −20° C.-100° C. (preferably 20°-50° C.).

The product of formula (I) can be isolated by filtering the precipitate formed in the reaction and can be purified either by recrystallising from a suitable solvent or by high performance liquid chromatography (HPLC).

The compound of formula (III) may be produced as described in the aforesaid European Patent Publications Nos. 59536, 61836 and 76030. A further process for making compounds of the invention in which R is a 1-alkenyl group is outlined in Scheme B:

Scheme B

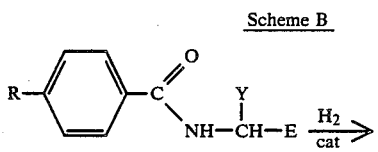

(Formula I
wherein R = 1-alkynyl)

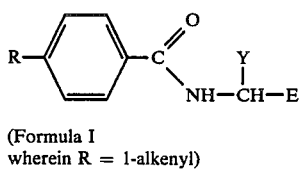

(Formula I
wherein R = 1-alkenyl)

In Scheme B a compound of formula (I) 1-alkenyl group may be produced by reducing a compound of formula (I) wherein R is a 1-alkynyl group with hydrogen gas in the presence of a catalyst such as palladium-on-carbon or the Lindlar catalyst, in a suitable solvent such as ethyl acetate or lower alkanols such as ethanol or methanol, (but preferably in ethyl acetate), and at a pressure of 1-20 atmospheres (preferably 1-5 atmospheres) and at a temperature of 0°-100° (preferably 20°-25° C.).

The product of formula (I) wherein R is a 1-alkenyl group may be isolated by filtering the catalyst and evaporating the solvent, and can be purified either by recrystallising the compound from a suitable solvent or by HPLC.

A further process for preparing compounds of the invention in which R is an ethynyl group is outlined in Scheme C:

Scheme C

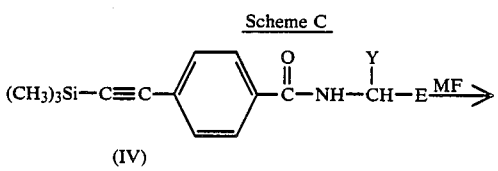

(IV)

-continued
Scheme C

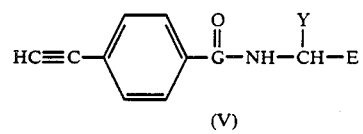

(V)

The compounds of formula (V) may be produced by reacting a compound of formula (IV) with an inorganic fluoride salt such as potassium fluoride, in a suitable solvent such as a lower alkanol (e.g. methanol or ethanol) or dimethylformamide or acetonitrile.

The required product (V) may be isolated by removal of the solvent and may be purified by recrystallisation or HPLC.

Compounds of the invention in which group E is a thiocarbamoyl radical may be prepared according to Scheme D:

Scheme D

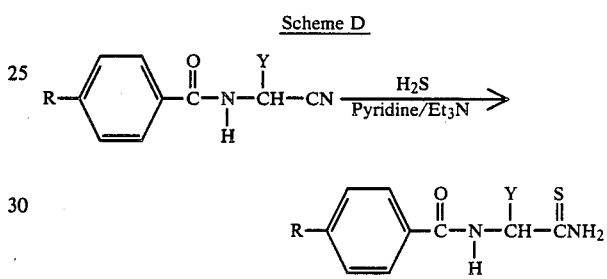

The reaction is conveniently carried out by passing gaseous H$_2$S through a solution of the nitrile in a suitable solvent such as toluene or pyridine in the presence of a suitable catalyst such as triethylamine. Usually the solution is externally cooled to 0°-10° C. If the product does not separate from the solution, it may be isolated by removal of the solvent. There will be other methods of making the compounds of the invention. For instance, it may be possible to adapt one or more of the several processes described in the previously mentioned European Patent Publications Nos. 59536, 61836 and 76030 or in European Patent Publication No. 144177 or UK patent specification No. 2146983. In particular, if the group R is not readily brominated or a brominated group R is desired, a process (which involves a bromination step) described in these aforesaid publications, may conveniently be used. Such a process is outlined in Scheme E:

Scheme E

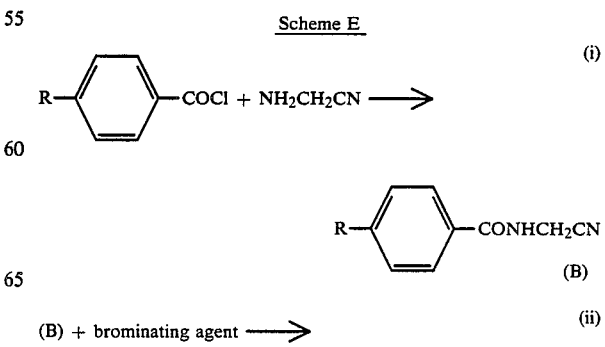

-continued
Scheme E

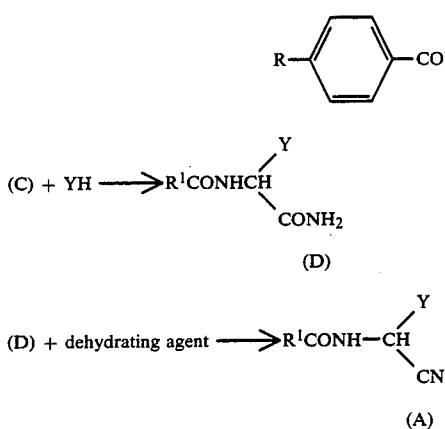

In step (i) of Scheme E, an acid chloride

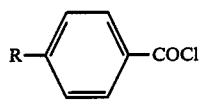

is reacted with aminoacetonitrile by a conventional procedure to obtain the compound (B). This is then reacted in step (ii) with a brominating agent (for example bromine in glacial acetic acid) to give the brominated and hydrated derivative (C). (Hydration may be avoidable depending on how the bromination is done—see, for example, EP-A-144177). In step (iii), the bromo compound (C) is reacted with a compound YH (in which Y is as previously defined but not 2-furyl) to obtain the carbamoyl compound (D) which is then treated with a dehydrating agent in step (iv) to convert it to the corresponding cyano compound (A).

For compounds in which Y is 2-furyl, reference is made to European patent publication No. 61836.

The amide derivatives of formula I, and compositions containing them, are active against certain fungal diseases, particularly,

*Plasmopora viticola* (downy mildew on vines),
*Cercospora arachidicola* on peanuts,
*Phytophthora infestans* (late blight on potatoes and tomatoes) and similar diseases.

A particularly valuable feature of the activity of the compounds of the invention is their systemic effect, ie. their ability to move in a plant to combat an infection or infestation remote from the site of initial application. Thus a derivative, or a composition containing it, may be applied to the soil surrounding the roots of a plant or to the seed or to other plant areas, eg. leaves, and be taken up by the plant through its roots, or other areas, to combat fungi locally or elsewhere on the plants.

As well as being fungicidally active the compounds exhibit plant growth regulating activity which may be manifested as, for example, by a stunting or dwarfing effect on the vegetative growth of woody and herbaceous mono- and di-cotyledenous plants. Such stunting or dwarfing may be useful, for example, in peanuts, cereals such as wheat and barley, oil seed rape, field beans, sunflowers, Potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied.

The compounds may be used directly for fungicidal and plant growth regulating purposes but are more conveniently formulated into compositions using a carrier or diluent. The invention thus provides a fungicidal or plant growth resulating composition comprising a compound of general formula (I) as hereinbefore defined, and an acceptable carrier or diluent therefor.

The invention also provides a method of combating fungi or regulating plant growth, which comprises applying to a plant, to a seed of a plant, or to the locus of the plant or seed, a compound as hereinbefore defined, or a composition containing the same. The compounds, can be applied in a number of ways. For example they can be applied, formulated or unformulated, directly to the foliage of a plant, to seeds or to other medium in which plants are growing or are to be planted. They can be sprayed on, dusted on or applied as a cream or paste formulation; or they can be applied as a vapour or as slow release granules. Application can be to an part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees Furthermore, the methods of the invention include preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler.

Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate their dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone and methylcyclohexanone, chlorinated hydrocarbons such as chlorobenzene and trichlorethane, and alcohols such as furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants eg. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal or plant growth regulating activity or which possess other fungicidal or plant growth regulating activity or insecticidal activity.

A fungicidal compound which may be present in the composition of the invention may be one which is capable of combating ear diseases of cereals (e.g. wheat) such as Septoria, Gibberella and Helminthosporium spp., seed and soil borne diseases and downy and powdery mildews on grapes and powdery mildew and scab on apple etc. By including another fungicide the composition can have a broader spectrum of activity than the compound of general formula (I) alone. Further the other fungicide may have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl aluminium, fenarimol, iprodione, procymidone, vinclozolin, penconazole, myclobutanil, RO151297, S3308, pyrazophos, ethirimol, ditalimfos, tridemorph, triforine, nuarimol, triazbutyl, guazatine, propiconazole, prochloraz, flutriafol, hexaconazole i.e. the chemical 1-(1,2,4-triazol-1-yl)-2-(2,4-dichlorophenyl)-hexan-2-ol, DPX H6573(1-(bis-4-fluorophenyl)methylsilyl)methyl)-1H-1,2,4-triazole, triadimefon, triadimenol, diclobutrazol, fenpropimorph, fenpropidine, chlorozolinate, diniconazol, imazalil, fenfuram, carboxin, oxycarboxin, methfuroxam, dodemorph, BAS 454, blasticidin S, Kasugamycin, edifenphos, kitazin p, cycloheximide, phthalide, probenazole, isoprothiolane, tricyclazole, pyroquilan, chlorbenzthiazone, neoasozin, polyoxin D, validamycin A, repronil, flutolanil, pencycuron, diclomezine, phenazin oxide, nickel dimethyldithiocarbamate, techlofthalam, bitertanol, bupirimate, etaconazole, streptomycin, cypofuram, biloxazol, quinomethionate, dimethirimol, 1-(2-cyano-2-methoxyiminoacetyl)-3-ethyl urea, fenapanil, tolclofosmethyl, pyroxyfur, polyram, maneb, mancozeb, captafol, chlorothalonil, anilazine, thiram, captan, folpet, zineb, propineb, sulphur, dinocap, binapacryl, nitrothalisopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Examples of suitable plant growth regulating compounds for use with the invention compounds are the gibberellins (e.g. GA$_3$, GA$_4$ or GA$_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-12-dihydropyridine-3-carboxylic a hydroxybenzonitriles (eg. bromoxynil), difenzoquat, benzoylprop-ethyl 3,6-dichloropicolinic acid, fenpentezol, inabenfide, triapenthenol and tecnazene.

The invention is illustrated by the following Examples, in which unless otherwise stated all parts and percentages are by weight and temperatures in degrees Centigrade. The Examples that describe chemical syntheses give details of the nuclear magnetic resonance (NMR) spectra of the compounds. The information given is the chemical shift ($\delta$) for each peak in the spectrum together with a symbol to indicate the nature of the peak, as follows: s(singlet); d(doublet); m(multiplet); q(quartet); t(triplet). The solvent used was fully deuterated dimethyl sulphoxide or deuterochloroform (CDCl$_3$). Information is also given on infra-red (IR) spectra of the compounds. The information given is the transmission for each peak together with a symbol to indicate the size of the peak; s(strong); w(weak).

EXAMPLE 1

This example illustrates the preparation of compound No 2 of Table I by Scheme A.

2-[4-(Prop-1-ynyl)-benzoylamino]-2-(1-pyrazolyl)-acetonitrile

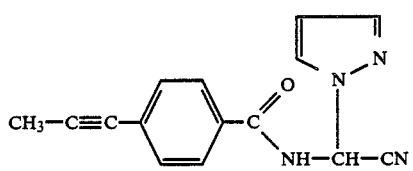

Propyne gas was bubbled into triethylamine (20 ml) until about 0.5 gm had been absorbed. To this solution was then added tetrakistriphenylphosphine palladium (100 mg) and 4-iodobenzoylamino-2-(1-pyrazolyl)-acetonitrile (1.0 gm) followed by cuprous iodide (50 mg) and the whole solution was stirred at room temperature for three hours. The thick precipitate was then filtered and dried to give a tan solid which was purified by preparative HPLC on Merck Kieselgel 9385 eluting with light petroleum: ethyl acetate (7:3) to give the product as a white crystalline solid (0.40 gm), mpt 185°–187° C.

IR (nujol)$v$: 3230 (s), 2250 (w), 2210 (w), 1650 (s) cm$^{-1}$.

NMR (d$^6$-DMSO)$\delta$: 2.04 (S,3H), 6.32 (M, 1H), 7.36–7.68 (M, 4H), 7.80–8.00 (M, 3H), 10.51 (S, 1H)

EXAMPLE 2

This example illustrates the preparation of compound No 5 of Table I by Scheme A.

2-[4-Trimethysilylethynyl benzoylamino)-2-ethoxy acetonitrile

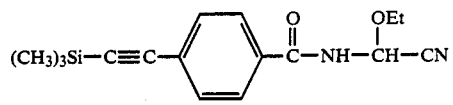

Cuprous iodide (50 mg) was added to a stirred mixture of trimethylsilylacetylene (0.30 gm), 4-iodobenzylamino -2-ethoxyacetonitrile (1.0 gm) and tetrakistriphenylphosphine palladium (100 mg) in triethylamine (10 ml) at room temperature. The mixture became warm and after 20 minutes was filtered through a short plug of alumina and silca gel, and washed through with ethyl acetate. The filtrate was washed with water, dilute hydrochloric acid, and then water again. It was dried over magnesium sulphate and the ethyl acetate was evaporated. The resultant yellow oil was purified by preparative HPLC on Merck Kieselgel 9385 eluting with light petroleum: ethyl acetate (8:2), to give the desired product as a white power (0.70 gm), mpt 134°–136° C.

IR (nujol)$v$: 3270 (s), 2160 (w), 1655 (s) cm$^{-1}$.

NMR (CDCl$_3$)$\epsilon$: 0.28 (s, 9H), 1.24 (t, 3H), 3.71 (q, 2H), 6.24 (d, 1H), 7.56 (d, 3H), 7.80 (d, 2H)

EXAMPLE 3

This example illustrates the preparation of compound no 4 of Table I by Scheme C.

2-(4-Ethynylbenzoylamino)-2-ethoxy acetonitrile

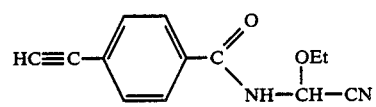

The trimethylsilyl acetylene (compound no 5 from Table I, 0.50 gm) was stirred at room temperature in ethanol 20 ml) with anhydrous potassium fluoride (0.12 gm) overnight. The ethanol was evaporated and the oily residue purified by preparative HPLC on Merck Kiesselgel 9385 eluting with light petroleum: ethyl acetate (17:3) to give the desired product as a white crystalline solid, (100 mg), mpt 104°–106° C.

IR (nujol)$v$: 3265 (s), 2100 (w), 1660 (s) cm$^{-1}$

NMR (CDCl$_3$)$\epsilon$: 1.24 (t,3H) 3.20 (s,1H) 3.47 (q,2H) 6.12 (d,1H) 7.40 (d,2H) 7.52–7.76 (m,3H)

EXAMPLE 4

This example illustrates the preparation of compound no 13 of Table I by Scheme B.

2-(4-Vinylbenzoylamino)-2-(1-pyrazolyl)-acetonitrile

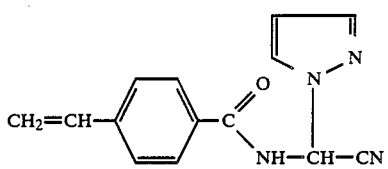

The 4-ethynyl compound (compound No. 1 from Table I, 0.10 gm) was hydrogenated with hydrogen gas at a pressure of 8 psi in ethyl acetate (10 ml) at room temperature over Lindlar catalyst (35 mg). After 45 minutes the theoretical amount of hydrogen had been taken up, and the reaction was worked up. The catalyst was filtered, and the ethyl acetate filtrate was evaporated, to give the desired product as a cream solid (100 mg), mpt 159°–161° C.

IR (nujol)ε: 3250 (s), 1650 (s) cm$^{-1}$.

NMR (d$^6$-DMSO)ε: 5.34 (d,1H), 5.91 (d, 1H), 6.32 (t, 1H), 6.76 (dd, 1H), 7.44–7.64 (M, 3H), 7.80–7.96 (M, 2H), 10.50 (S, 1H)

EXAMPLE 5

This Example illustrates a composition according to the invention which comprises an emulsifiable concentrate. The following ingredients are thoroughly mixed to give a solution.

| Compound No. 1 of Table I | 10% |
| --- | --- |
| Ethylene dichloride | 40% |
| Calcium dodecylbenzenesulphate | 5% |
| "Lubrol" L | 10% |
| "Aromasol" H | 35% |

EXAMPLE 6

A composition in the form of grains readily dispersible in a liquid, e.g. water, is prepared by grinding together the first three ingredients in the presence of added water and then mixing in the sodium acetate. The resultant mixture is dried and passed through a British Standard mesh sieve, size 44–100, to obtain the desired size of grains.

| Compound No. 2 of Table I | 50% |
| --- | --- |
| "Dispersol" T | 25% |
| "Lubrol" APN 5 | 1.5% |
| Sodium acetate | 23.5% |

EXAMPLE 7

The following ingredients are ground together to produce a powder formulation readily dispersible in liquids.

| Compound No. 3 of Table I | 45% |
| --- | --- |
| "Dispersol" T | 5% |
| "Lissapol" NX | 0.5% |
| "Cellofas" B600 | 2% |
| Sodium acetate | 47.5% |

EXAMPLE 8

The active ingredient is dissolved in acetone and the resultant liquid is sprayed on to the granules of china clay. The solvent is then allowed to evaporate to produce a granular composition.

| Compound No 1 of Table I | 5% |
| --- | --- |
| China clay granules | 95% |

EXAMPLE 9

A composition suitable for use as a seed dressing is prepared by mixing the following three ingredients.

| Compound No 2 of Table I | 50% |
| --- | --- |
| Mineral oil | 2% |
| China clay | 48% |

EXAMPLE 10

A dusting powder is prepared by mixing the active ingredient with talc.

| Compound No 3 of Table I | 5% |
| --- | --- |
| Talc | 95% |

EXAMPLE 11

A Col formulation is prepared by ball-milling the constituents set out below and then forming an aqueous suspension of the ground mixture with water.

| Compound No 1 of Table I | 40% |
| --- | --- |
| "Dispersol" T | 10% |
| "Lubrol" APN5 | 1% |
| Water | 49% |

EXAMPLE 12

A dispersible powder formulation is made by mixing together the ingredients set out below and then grinding the mixture until all are thoroughly mixed.

| Compound No 2 of Table I | 25% |
| --- | --- |
| "Aerosol" OT/B | 2% |
| "Dispersol" A.C. | 5% |
| China clay | 28% |
| Silica | 40% |

EXAMPLE 13

This Example illustrates the preparation of a dispersible powder formulation. The ingredients are mixed and the mixture then ground in a comminution mill.

| Compound No 3 of Table I | 25% |
| --- | --- |
| "PERMINAL" BX | 1% |
| "Dispersol" T | 5% |
| Polyvinylpyrrolidone | 10% |
| Silica | 25% |
| China clay | 34% |

EXAMPLE 14

The ingredients set out below are formulated into a dispersible powder by mixing then grinding the ingredients.

| | |
|---|---|
| Compound No 1 of Table I | 25% |
| "Aerosol" OT/B | 2% |
| "Dispersol" A | 5% |
| China clay | 68% |

In Examples 5 to 14 the percentage proportions of the ingredients are by weight. The Examples are repeated using, as active ingredient, the other compounds of Table I.

There now follows an explanation of the compositions or substances represented by the various Trade Marks and Trade Names mentioned above.

LUBROL L: a condensate of nonyl phenol (1 mole) with ethylene oxide (13 moles).

AROMASOL H: a solvent mixture of alkylbenzenes

DISPERSOL T AND AC: a mixture of sodium sulphate and a condensate of formaldede with sodium naphthalene sulphonate LUBROL ApN 5: a condensate of nonyl phenol (1 mole) with ethylene oxide (5.5 moles)

CELLOFAS B600: a sodium carboxymethyl cellulose thickener.

EXAMPLE 15

Compounds Nos. 1-6, 8 and 13 were tested against a variety of mainly foliar fungal diseases of plants. The technique was as follows:

For all tests, plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliar diseases, solutions and suspensions (100 ppm ai) were sprayed on the foliage and applied to the roots of the plant via the soil. The sprays were applied to maximum retention and the root drenches to a final concentration equivalent to approximately 40 ppm ai/dry soil. Tween 20, to give a final concentration of 0.05%, was added when the sprays were applied to cereals (ai means "active ingredient").

Most were protectant tests where the compound was applied to the soil and roots and to the foliage one or two days before the plant was inoculated with the pathogen. However, in the case of the test against *Erysiphe graminis hordei* the treatment was eradicative and the compounds were applied one day after inoculation.

The foliar pathogens were applied by spraying spore suspensions onto the leaves of the test plants.

After inoculation, the plants were placed in an appropriate environment to allow infection to proceed and then incubated until the disease was ready for assessment. The period between inoculation and assessment varied from four to fourteen days according to the disease and the environment.

Disease control was recorded using the following grading system:
4 = no disease
3 = trace to 5% of disease on untreated plants
2 = 6–25% of disease on untreated plants
1 = 26–59% of disease on untreated plants
0 = 60–100% of disease on untreated plants The results are shown in Table II below.

TABLE II

| Compound No. of Table I | Pi | Pr | Egh | Vi | Po | Ca | Pv | Rs | Xo |
|---|---|---|---|---|---|---|---|---|---|
| 1 | — | 0 | 0 | 0 | 0 | 4 | 4 | 0 | 0 |
| 2 | — | 0 | 0 | 0 | 0 | 4 | 4 | 0 | 0 |
| 3 | — | 0 | 0 | 0 | 0 | 4 | 3 | 0 | 0 |
| 4 | — | 0 | 0 | 0 | 0 | 2 | 4 | 0 | 0 |
| 5 | — | 0 | 0 | 0 | 0 | 0 | 4 | 0 | 0 |
| 6 | — | 0 | 0 | 0 | 0 | 0 | 4 | 0 | 0 |
| 8 | 4 | 0 | 0 | * | 0 | 0 | 4 | 0 | 0 |
| 13 | — | 0 | 0 | 0 | 0 | 3 | 4 | 0 | 0 |

Pi = *Phytophthora infestans* (Late blight on tomatoes)
Pr = *Puccinia recondita* (Rust on wheat)
Egh = *Erysiphe graminis* (Powdery mildew on barley)
Vi = *Venuria inaequalis* (Scab on apples)
Po = *Piricularia oryzae* (Blast on rice)
Ca = *Cercospora arachidicola* (Leaf spot on peanuts)
Pv = *Plasmopara viticola* (Downy mildew on vines)
Rs = *Rhizoctania solani* (Damping-off disease)
Xo = *Xanthomonas oryzae* (Blight on rice)
*Grading not possible owing to phytotoxic effect.
— Not tested

EXAMPLE 16

Compounds Nos 1 to 6 and 13 were tested on a whole plant screen for plant growth regulator activity against five species of plant. The plant species used in this screen are presented in Table III with the leaf stage at which they were sprayed.

A formulation of each chemical was applied at 4000 ppm (4 kg/ha in a 1000 l/ha field volume) using a track-sprayer and a SS8004E (Teejet) nozzle.

After spraying the plants were grown in a glasshouse with 25° C. day/22° C. night temperatures. The exception to this were the temperate cereals, wheat and barley, which were grown in 13°–16° C. day/11°–13° C. night temperatures. Supplementary lighting was supplied when necessary to provide an average photoperiod of 16 hours (14 hours minimum).

After 2–6 weeks in the glasshouse, depending on species and time of year, the plants were visually assessed for morphological characteristics against a control plant sprayed with a 'blank' formulation. The results are presented in Table IV.

TABLE III

PLANT MATERIAL USED FOR WHOLE PLANT SCREEN

| Species | Code | Variety | Growth Stage at Treatment | No. Plants per 3" pot | Compost Type |
|---|---|---|---|---|---|
| Barley | BR | Atem | 1–1.5 leaves | 4 | JIP* |
| Wheat | WW | Timmo | 1–1.5 leaves | 4 | JIP |
| Maize | MZ | Earliking | 2¼ leaves | 1 | PEAT |
| Apple | AP | Red Delicious | 4–5 leaves | 1 | JIP |
| Rice | RC | Ishikari | 2–2½ leaves | 4 | JIP |

JIP* = John Innes Potting Compost.

TABLE IV

| Compound No. | Plant Species | R | G | A | T | I | P |
|---|---|---|---|---|---|---|---|
| 1 | WW | 3 | 2 | 0 | 0 | 3 | 0 |
|   | BR | 1 | 0 | 1 | 1 | 1 | 0 |
|   | RC | 1 | 0 | 0 | 0 | 1 | 0 |
|   | AP | 3 | 0 | 1 | 0 | 3 | 0 |
|   | MZ | 0 | 0 | 1 | 0 | 0 | 0 |
| 2 | WW | 0 | 0 | 0 | 0 | 0 | 0 |
|   | BR | 0 | 0 | 0 | 0 | 0 | 0 |
|   | RC | 0 | 0 | 0 | 0 | 0 | 0 |
|   | AP | 0 | 1 | 0 | 0 | 0 | 0 |
|   | MZ | 0 | 0 | 0 | 0 | 0 | 0 |
| 3 | WW | 1 | 0 | 0 | 0 | 1 | 0 |

TABLE IV-continued

| Compound No. | Plant Species | R | G | A | T | I | P |
|---|---|---|---|---|---|---|---|
|  | BR | 0 | 0 | 0 | 0 | 0 | 0 |
|  | RC | 0 | 0 | 0 | 0 | 0 | 0 |
|  | AP | 0 | 0 | 0 | 0 | 0 | 0 |
|  | MZ | 0 | 0 | 0 | 0 | 0 | 0 |
| 6 | WW | 0 | 0 | 0 | 0 | 0 | 0 |
|  | BR | 0 | 0 | 0 | 1 | 0 | 0 |
|  | RC | 0 | 0 | 0 | 0 | 0 | 0 |
|  | AP | 0 | 0 | 0 | 0 | 0 | 0 |
|  | MZ | 0 | 0 | 0 | 0 | 0 | 0 |

Key to Table IV
R = Retardation
G = Greening effect
A = Apical damage
T = Tillering or side shooting
I = Interligular or internodal length reduction
P = Phytoxicity
All effects are scored visually on a 1-3 basis where
1 = 10-30%
2 = 31-60%
3 = 61-100%
Zero means less than 10% effect.

We claim:

1. A compound of the general formula (I):

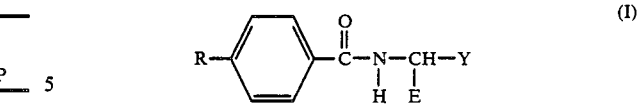

wherein
R is $C_2-C_4$ alkenyl or $C_2-C_4$ alkynyl, both optionally substituted by lower alkyl, halogen or tri lower alkylsilyl;
E is CN or $CSNH_2$; and
Y is 1-pyrazolyl or 2-furyl.

2. A compound according to claim 1, wherein R is selected from the group 1-($C_2-C_4$) alkenyl and 1-($C_2-C_4$) alkynyl optionally substituted by trimethylsilyl; E is CN or $CSNH_2$ and Y is 1-pyrazolyl or 2-furyl.

3. A compound according to claim 1, wherein R is ethynyl optionally substituted by trimethylsilyl or prop-1-ynyl, Y is 1-pyrazolyl, and E is CN.

4. A compound according to claim 1 wherein Y is 1-pyrazolyl, E is CN and R is C≡CH, $CH_2$=CH, C≡$CCH_3$ or C≡$CSi(CH_3)_3$.

5. A fungicidal or plant growth regulatory composition comprising as an active ingredient a fungicidally effective or plant growth regulating amount of a compound according to claim 1 and a carrier or diluent therefor.

6. A method of combating fungi or regulating plant growth which comprises applying to a plant, to the seed of a plant or to the locus the plant or seed a fungicidically effective or plant growth regulating amount of a compound according to claim 1.

* * * * *